United States Patent
Layton

(10) Patent No.: US 8,784,104 B2
(45) Date of Patent: Jul. 22, 2014

(54) DENTAL IMPLANT SYSTEM AND METHOD OF USE

(76) Inventor: Grant Layton, Carlsbad, CA (US)

( * ) Notice: Subject to any disclaimer, the term of this patent is extended or adjusted under 35 U.S.C. 154(b) by 0 days.

(21) Appl. No.: 13/481,819

(22) Filed: May 26, 2012

(65) Prior Publication Data

US 2012/0231418 A1 Sep. 13, 2012

Related U.S. Application Data

(63) Continuation of application No. 12/616,756, filed on Nov. 11, 2009, now Pat. No. 8,246,870.

(60) Provisional application No. 61/182,967, filed on Jun. 1, 2009.

(51) Int. Cl.
*A61C 8/00* (2006.01)
*A61C 13/00* (2006.01)

(52) U.S. Cl.
CPC ............. *A61C 8/005* (2013.01); *A61C 13/0004* (2013.01); *A61C 8/0056* (2013.01); *A61C 8/0069* (2013.01)
USPC ........................................ 433/173

(58) Field of Classification Search
USPC ........................................ 433/173
See application file for complete search history.

(56) References Cited

U.S. PATENT DOCUMENTS

| | | | | |
|---|---|---|---|---|
| 3,934,347 A | * | 1/1976 | Lash et al. | 433/173 |
| 5,562,450 A | * | 10/1996 | Gieloff et al. | 433/223 |
| 6,273,720 B1 | | 8/2001 | Spalten | |
| 2008/0241789 A1 | * | 10/2008 | Mundorf | 433/173 |

FOREIGN PATENT DOCUMENTS

WO 2006084346 8/2006

* cited by examiner

*Primary Examiner* — Larry Thrower
(74) *Attorney, Agent, or Firm* — Themis Law

(57) ABSTRACT

A dental implant system includes an implant having a well, an abutment having a post shaped to be received in the well, and a collar modifiable to the gingival anatomy and the tooth restoration anatomy. Both the implant and the abutment are made from a millable ceramic, and the abutment post and/or the implant well have grooves carved therein. In one embodiment, the implant and the abutment are joined one to the other with a retentive elastomeric product containing micro-bubbles and/or micro-spacers. The dental implant system may be produced using a computer-readable medium containing instructions for analyzing surface data and X-ray data, for developing contour data of the implant and of the abutment according to the anatomy of the patient, and for generating machine instruction for milling the implant and the abutment from blocks of the millable ceramic.

17 Claims, 10 Drawing Sheets

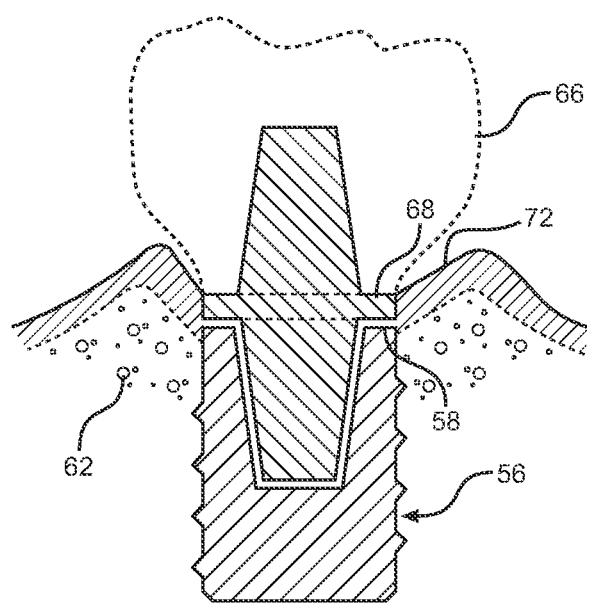
FIG. 7
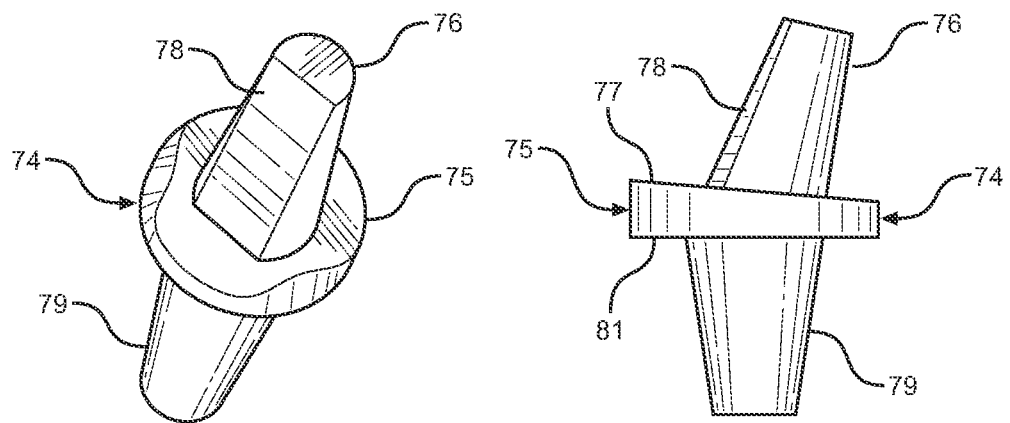
FIG. 8A  FIG. 8B

DENTAL IMPLANT SYSTEM AND METHOD OF USE

CROSS-REFERENCE TO RELATED APPLICATIONS

The present application is a continuation of U.S. application Ser. No. 12/616,756 having a filing date of Nov. 11, 2009, which claims priority to U.S. provisional application No. 61/182,967 having a filing date of Jun. 1, 2009, the entireties of which are hereby incorporated by reference.

FIELD OF THE INVENTION

The present invention concerns a dental implant system made from a millable ceramic material and related methods of use. More particularly, the present invention concerns a dental implant system, in which an implant having a well engages an abutment having a post and a collar that extends outwardly to be flush with the outer surface of the implant. In one embodiment, the implant and the abutment are joined one to the other with a retentive elastomeric product, which contains micro-bubbles and spacer elements and which fills grooves provided on the abutment post and/or the implant well.

BACKGROUND OF THE INVENTION

A dental implant system is an artificial tooth root replacement, which is used in prosthetic dentistry to support restorations that resemble a tooth or a group of teeth. An implant system typically includes an implant or base, which is surgically placed in the jaw of a patient, and an abutment or extension, which extends from the implant to support a restoration.

Known implant systems are essentially of two types. Referring to FIG. 1, a first type of implant system 2 in the prior art includes an implant 4, which is placed in a hole bored in the recipient bone, and an abutment 8, which operates as a support for a dental restoration and which may include a metallic interface 6 extending downward to engage implant 4. Implant system 2 also includes a screw-type device 10 engaging abutment 8, abutment interface 6 and implant 4 longitudinally.

A second type of implant system 10 is illustrated in FIG. 2 and includes an implant 12, which is placed in a hole bored in the recipient bone and which has a sloping shoulder 14. Implant system 10 further includes an abutment 13, which supports restoration 16 (shown in the form of a front tooth) and which has a locking taper 18 that is force-fitted into a well in the inner portion of implant 12.

Implants in the prior art (such as those depicted in FIGS. 1 and 2) are generally made from titanium due to the strength and biocompatibility properties of this metal. In addition, titanium can be successfully fused into the surrounding bone when osteoblasts move on and into its surface. This process is generally termed "integration" or "osseointegration" and produces a strong anchoring that prevents an independent movement of the implant.

Unfortunately, metal implants also have a number of drawbacks, which include:

1. Metal implants are mostly made not from pure titanium, but from titanium alloys to improve ease of machining. For example, Grade 5 titanium is sometime employed, which is an alloy that contains aluminum and vanadium. Some of those titanium alloys contain elements that are potentially toxic elements.

2. Metal implants may cause "oral galvanism," which is a toxic effect caused by a galvanic current generated from the transport of metal ions through the saliva from the implant to another metallic restoration such as a different implant, a filling, a crown or an orthodontic device. As a consequence, the rate of corrosion (or dissolution) of a metal-based restoration is increased, leading to dispersion of metal ions and related oxides in the patient's body and to sensitivity, inflammations, allergies and autoimmune diseases.

3. The attachment of the internal screw (for example, screw 10 of FIG. 1) may fail. The screw may loosen, break, and become a source of bacteria due to manufacturing tolerances between the screw and the implant, leading to a rejection or to a supporting bone failure for the entire implant.

4. Current implant designs include a number of curvatures and recesses that may house bacterial colonies and cause infections and inflammations for lack of access and proper dental hygiene.

5. Metal implants are rigid attachments that are unsuitable for bridging to a natural tooth, which by its nature is slightly mobile. Therefore, there is an inherent incompatibility between a metal implant and a neighboring natural tooth. In some instances, a restoration (for example, an artificial crown) may break due to the inflexibility in the implant.

6. Metal implants are dark in color and tend to show through gum tissue, making them cosmetically unsightly.

7. Metal implants are manufactured and sold in many sizes and the restoring dentist must carry a significant inventory, leading to a sizable monetary investment in implants, abutments, accessories, instruments, etc.

8. The dentist's choice of implant and abutment designs is limited to what is commercially available, limiting the usefulness of the implant and the creativity of the restoring dentist.

In order to decrease rigidity, metal implants have been proposed that include a plastic element providing the abutment with some degree of movement in relation to the implant. Such a plastic element not only adds to the complexity of the implant, but unfortunately tends to fail after a few months of service.

Recent research in dental implantology has focused on the use of zircon dioxide ($ZrO_2$, generally identified in the dental field as zirconia) for the manufacture of dental implants. Zirconia is a high-strength ceramic material that can be milled to shape in a dentist's office using especially designed CAD-CAM machines. In addition, zirconia is highly biocompatible and is more cosmetically pleasing due to its bright, tooth-like color.

The designs of zirconia implants and abutments that have been proposed to date are essentially based on existing metal implant designs. In particular, no implant and abutment designs have been proposed that maximize the properties of zirconia and that resolve or at least minimize the drawbacks associated with current metal implant systems.

Therefore, it would be desirable to provide a dental implant system that is made entirely from zirconia and that maximizes the properties of zirconia.

It would also be desirable to have a dental implant system that is made with a reduced number of components than implant systems of the prior art.

It would further be desirable to have a dental implant system that can be custom-milled to shape in a dental office or at an outside dental lab.

It would further be desirable to have a dental implant system having contours that minimize the risk of bacterial infections and that are adaptable for use in different positions within the mouth of the patient, for example, in the front area of the mouth.

It would further be desirable to have a dental implant system that allows some degree of movement to the supported restoration in a manner similar to natural teeth.

SUMMARY OF THE INVENTION

In its most basic configuration, a dental implant system according to the present invention includes an implant and abutment each made from a millable ceramic, such as zirconia either in pure form or in the form of a composition.

The implant is defined by a cylindrical outer surface and by an inner surface shaped to form a well, which are connected one to the other by an annular upper surface.

The abutment includes a lower post shaped to engage the well of the implant and an upper stump designed to carrying a dental restoration. A collar is also provided at the transition area between the stump and the post and, in one embodiment, has a lower outer perimeter substantially equal to the outer perimeter of the upper surface of the implant, and an upper outer perimeter substantially equal to the outer perimeter of the margin of the restoration. The collar and the upper surface of the implant may be flat or contoured to fit the specific anatomy of a patient and are assembled in facing relationship.

In one embodiment of the invention, the post of the abutment includes one or more grooves that extend laterally in relation to the longitudinal axis of the post, for example, the one or more grooves may be perpendicular to or extend spirally around the post. The one or more grooves form annular cavities to be filled by a retentive product (which in one embodiment may be a retentive elastomeric product) that creates a mechanical lock between the abutment and the well, such to counteract tensile and compressive forces applied to the abutment. A "retentive elastomeric product," "retentive elastomer," or "retentive resilient product" is defined herein as a polymeric product, which has the property of elasticity and/or resiliency and which may be of any chemistry providing such property. This product may or may not have chemical or chemical-physical adhesive properties.

The well may also include one or more recesses, which may or may not be disposed in facing relationship with at least one of the grooves defined in the post, so to jointly create one or more toroidal cavities.

In one embodiment, one or more longitudinal grooves are carved in the post of the abutment. Such longitudinal grooves may be arranged symmetrically in relation to the longitudinal axis of the post. In addition, one or more longitudinal recesses may be carved in the well. The longitudinal grooves and recesses become also filled with the retentive product. Moreover, the longitudinal recesses may be used by the dentist as guides to place the implant in the alveolar bone by mating the recesses with protrusions on a tool used to insert the implant into the bone.

When the retentive product has elastomeric properties, it may include micro-bubbles that provide the desired elastic properties and allow a degree of movement of the supported restoration similar to that of a natural tooth. Micro-spacers may also be included that define a controlled gap between the well and the post. Preferably, the micro-spacers are flexible filled micro-spheres, micro-rods or micro-balloons of uniform diameter.

The outer surface of the implant may include a plurality of ridges that extend laterally, and a bottom portion that is tapered to produce a conical or ogival shape. The upper portion of the implant may have an enhanced diameter by flaring outwardly in the direction of the upper surface of the implant, in a configuration similar to the head of a wood screw.

The stump of the abutment may be angled in relation to the post and may include one or more generally flat surfaces that oppose rotation of a tooth restoration affixed to the stump.

The invention also relates to a computer-readable medium that carries one or more sequences of instructions for digital imaging and design of a dental implant system, and for providing instructions to a dental CAD/CAM milling machine. In one embodiment, execution of the sequences of instructions generates an analysis of surface and X-ray data provided by integration software that produces a digital model of a jaw of the patient, and the development of contour data both for the implant and for the abutment to suit a specific anatomy. Machine instructions are also provided for milling the implant and the abutment from blocks of the millable ceramic. The software according to the invention enables a restoring dentist to produce implants and abutments of desired shapes and when needed, providing the dentist with total flexibility and minimizing the dentist's inventory. Moreover, the invention may be embodied as an implant system that includes an implant placed at extraction, also identified as an "immediate implant."

An implant system according to the invention may also include a healing cap for covering the implant after placement of the implant in a patient. In one embodiment, the healing cap releases an antibiotic composition.

Methods of use of a dental implant system are also disclosed herein.

BRIEF DESCRIPTION OF THE DRAWINGS

The drawings constitute a part of this specification and illustrate exemplary embodiments of the invention. It is to be understood that in some instances various aspects of the invention may be shown exaggerated or enlarged to facilitate understanding.

FIG. 5A is a detail view of an alternate configuration of the implant system of FIG. 3, while

FIG. 6A illustrates an implant according to this variant before placement, and FIGS. 6B and 6C illustrate the implant system after placement and supporting a front tooth.

FIG. 7 illustrates an implant system according to invention after implantation into a patient's oral cavity.

FIGS. 8A-8B are respectively perspective and elevational views of a variant of the abutment of FIG. 3 having an angled stump, a collar with variable thickness and perimeter, and a flat face.

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1:
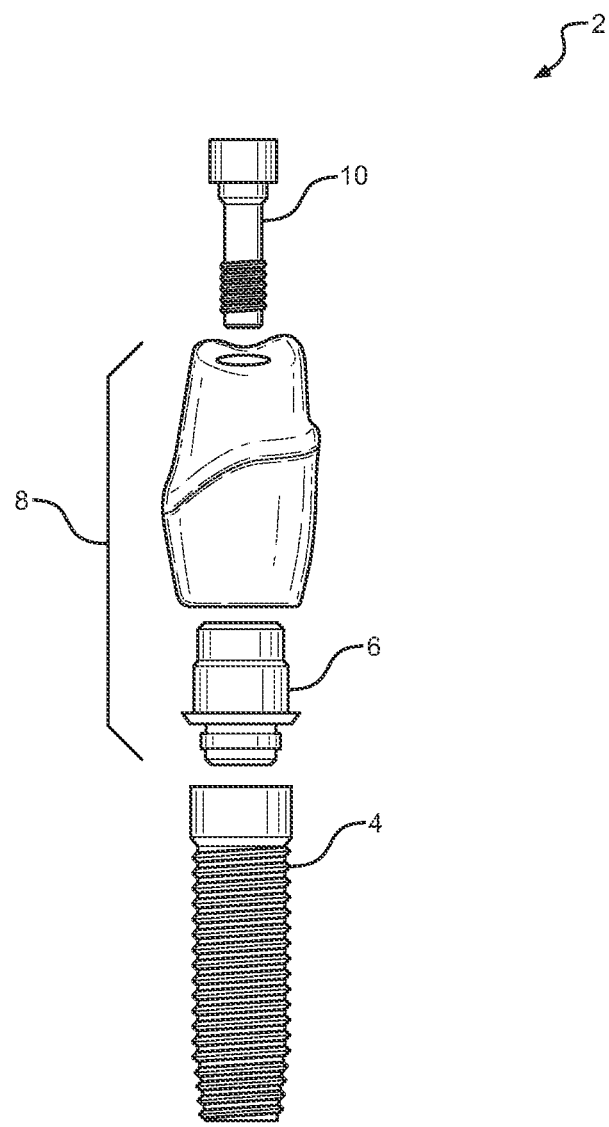
FIG. 1 illustrates a first implant system in the prior art.
Figure 2:
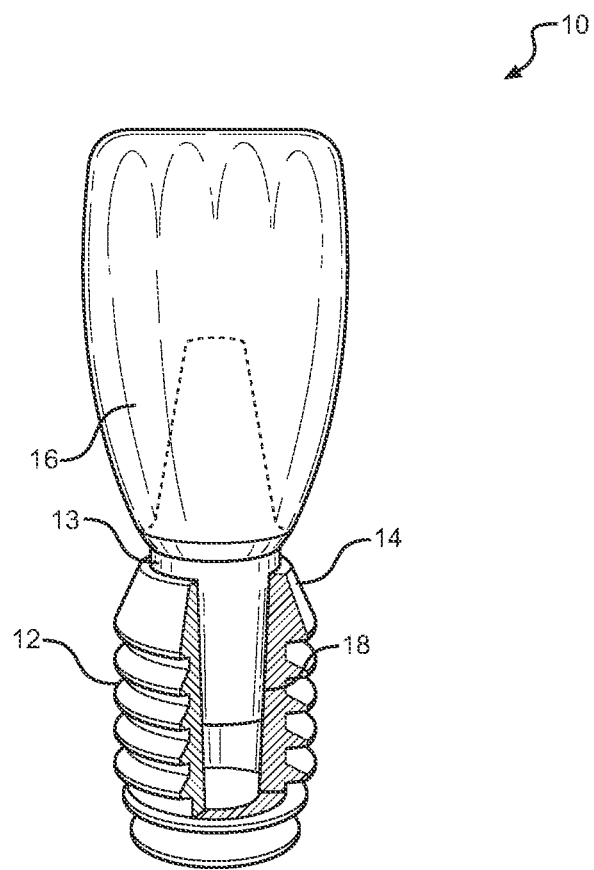
FIG. 2 illustrates a second implant system in the prior art.
Figure 3:
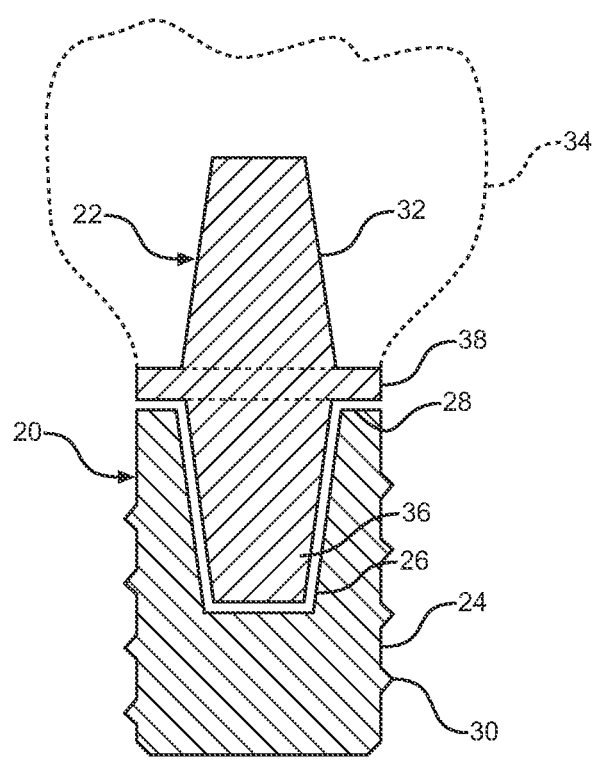
FIG. 3 is a cross-sectional view of an implant system according to the invention.

Referring first to FIG. 3, an implant system according to the principles of the invention includes an implant 20 and an abutment 22. Both implant 20 and abutment 22 are made from a millable ceramic such as zirconia. "Made from a millable ceramic" is meant to describe a product made from a pure form of the millable ceramic (for example, from pure zirconia) or from a composition containing the millable ceramic. For the sake of brevity, the embodiments described hereinafter will be disclosed using zirconia as the millable ceramic. Zirconia implant systems offer a number of advantages over traditional titanium implant systems, as previously explained and as further explained in greater detail hereinbelow.

Implant 20 has a cylindrical shape with an outer surface 24 and an inner surface, which extends longitudinally inside implant 20 to define an inwardly tapered well 26 having, in this embodiment, the shape of a truncated cone. In other embodiments, the well may have different shapes. Outer surface 24 and well 26 are connected by an upper surface 28, which has an annular shape.

Figure 4:
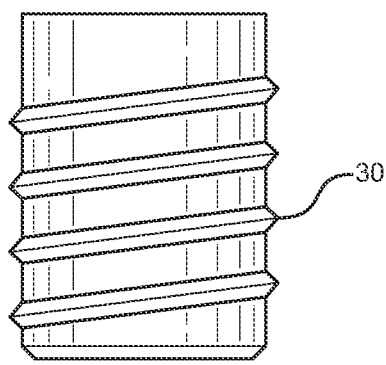
FIG. 4 is a perspective view of the implant of FIG. 3.

Outer surface 24 may be smooth or porous and have a plurality of ridges 30 extending outwardly. The plurality of ridges 30 increase the area of integration between implant 20 and the surrounding bone. When implant 20 is to be screwed in an opening drilled in the jaw of the patient, a single ridge may be disposed spirally around outer surface 24, as shown in FIG. 4, in a pattern comparable to the thread of a screw. These surface patterns of outer surface 24 are known to a person skilled in the art and will not be discussed in additional detail herein.

Still referring to FIG. 3, abutment 22 includes a stump 32, which extends upwardly from implant 20 and is designed to support a dental restoration (for example, an artificial crown 34). Abutment 22 also includes a post 36, which extends downwardly into well 26 and is shaped to mirror well 26. Preferably, post 36 and well 26 are shaped such that, when post 36 engages well 26, a gap or interstice is defined between post 36 and well 26 for placement of a dental cement or of a flexible product that provides not only a mechanical lock, but also shock-absorbing properties as explained in greater detail hereinafter. Such gap or interstice may be of even thickness, or may be of even thickness between the lateral walls of post 36 and well 26 and be thicker between the bases of post 36 and well 26. While both well 26 and post 36 are illustrated as having the shapes of truncated cones, well 26 and post 36 may also have a variety of other matching shapes.

A collar 38 is provided between stump 32 and post 36 and may be shaped with different contours, for example, like a flange extending outwardly of abutment 22. The perimetric extension of collar 38 at its base is equal to that of upper surface 28, such that, after coupling implant 20 with abutment 22, the lower surface of collar 38 has a perimeter that is flush with the upper periphery of implant 20. The retentive product disposed between post 36 and well 26 is also disposed between upper surface 28 and the lower surface of collar 38. The combination of the flush joint and of the retentive product between upper surface 28 and collar 38 eliminates or at least reduces the development of bacterial colonies at the joint between implant 20 and abutment 22, and, when the retentive product has elastomeric properties, it provides a shock-absorbing effect to the supported restoration, resolving problems affecting implant systems in the prior art.

In addition, collar 38 provides a support base for artificial crown 34. Preferably, the bottom (also identified as margin in the trade) of artificial crown 34 is shaped to match the upper surface of collar 38 and be flush with the upper and lateral surface of collar 38, preventing or at least reducing the development of bacterial colonies between crown 34 and abutment 22, and also facilitating a proper dental hygiene (for example, flossing). Therefore, such a construction would provide a flush structure that includes the margin of crown 34, the lateral surface of collar 38 of abutment 22, and upper outer surface 24 of implant 20.

Figure 5A:
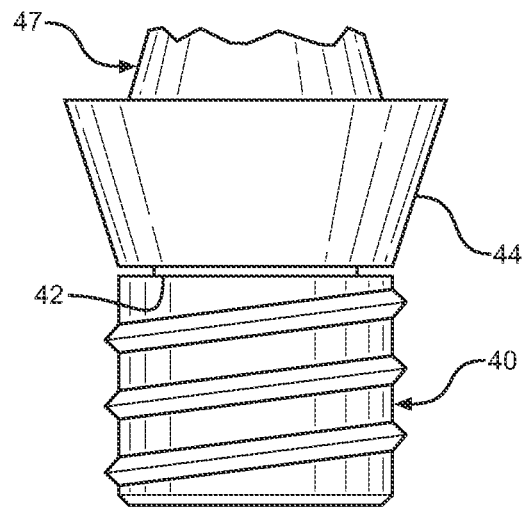
Figure 12:
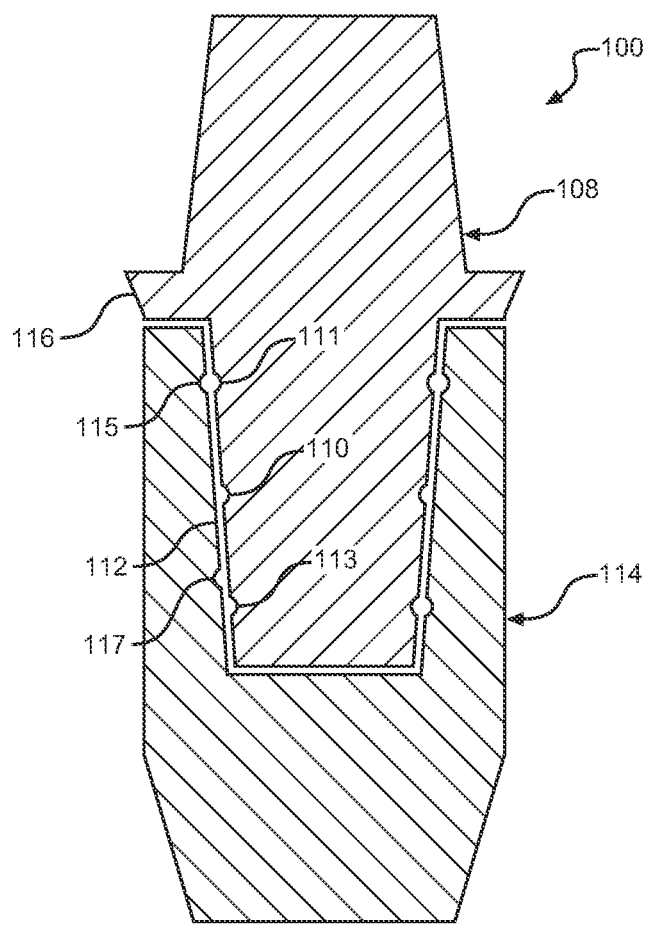
FIG. 12 is a cross-sectional view of a variant of the implant system of FIG. 10, which has a flaring collar and a different arrangement of the grooves in the abutment post and of the recesses in the implant well.

In other embodiments of the invention, the collar may flare outwardly, for example, have an upper portion that is larger than the diameter of the implant, creating a longitudinally divergent profile like collar 44 of FIG. 5A and 116 of FIG. 12. The upper and lower surfaces of collar 116 may be connected by a lateral circumferential wall that is either cylindrical, conical or have a variety of other shapes.

The height (that is, the longitudinal extension) of collar 38 may also vary and can be calculated by the restoring dentist based on thickness measurements of bone and gum levels. The outer perimeter of the upper face of collar 38 may also be shaped as desired by the restoring dentist such to have a shape that matches the bottom or margin of the supported restoration while the lower face of the collar 38 has a same or different face that matches upper surface of the implant, as shown in FIGS. 8A-8B.

In particular, FIGS. 8A-8B illustrate an abutment 74 having a collar 75, which has an upper face 77 that has a general shape to match the transverse anatomic profile of a bicuspid tooth and a lower face 81 that has a circular shape to match the upper surface of the implant which supports abutment 74. In addition, collar 75 has a longitudinal profile that is wedge-shaped to adapt to the anatomy of the patient and the specific positioning of the implant system. Such possible variations of collar 75 both in the horizontal and vertical directions illustrate an important feature of the present invention, that collar 75 is infinitely modifiable and is adaptable to the requirements of varying tissue height and tooth size and shape. A person skilled in the art will appreciate that infinitely modifiable collar 75 can have an upper face 77 mimicking the transverse anatomic profile of any tooth or restoration as well as a varying height. As an example, tooth size adaptability allows the same size implant to conform to a bicuspid sized tooth or to a molar tooth while conserving the natural tooth anatomy of these very different sized teeth. As another example, the infinitely modifiable collar allows for extreme adaptability in front teeth restoration, providing cosmetic results heretofore unattainable. The infinitely modifiable collar can be developed and produced with dental CAD/CAM equipment and the related software, as explained in greater detail hereinbelow.

Figure 5B:
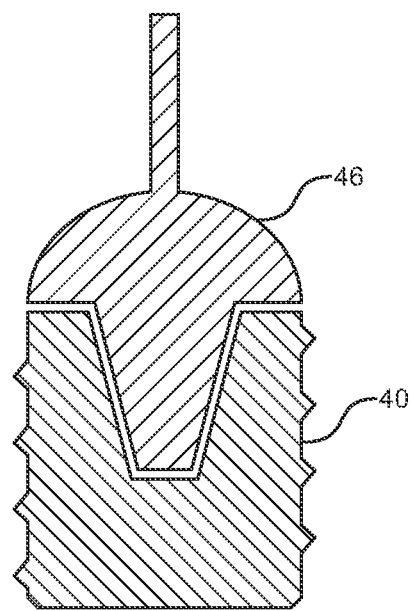
FIG. 5B illustrates the implant of FIG. 3 coupled with a healing cap.

FIG. 5A illustrates a detail of a variant, in which upper surface 42 of implant 40 faces collar 44 of abutment 47 that has increased thickness and that flares outwardly in comparison to collar 38 to conform to gum thickness of the patient and to achieve a best fit with the morphology of the mouth and supported tooth. FIG. 5B illustrates instead implant 40 coupled with a healing cap 46 after positioning in the alveolar bone, as described in greater detail hereinafter.

Figure 6A:
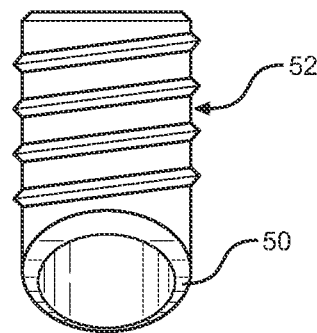
FIGS. 6A-6C illustrate a variant of the embodiment of FIG. 3, in which opposing surfaces of the implant and of the abutment collar are curved. In particular.
Figure 6B:
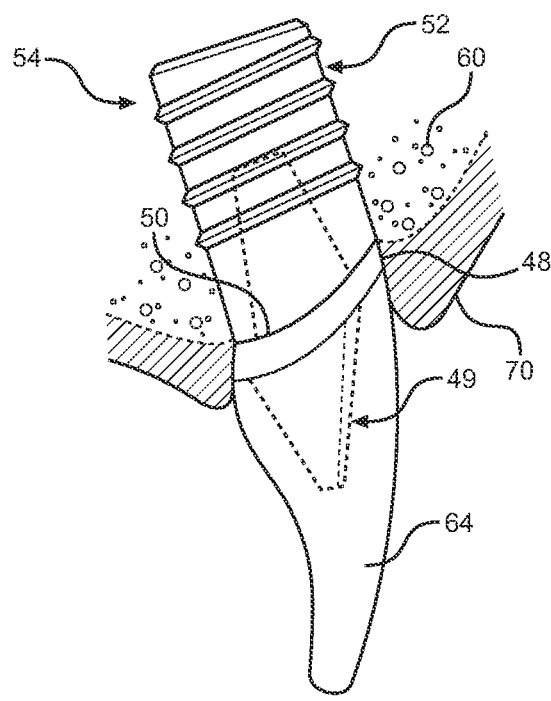
Figure 6C:
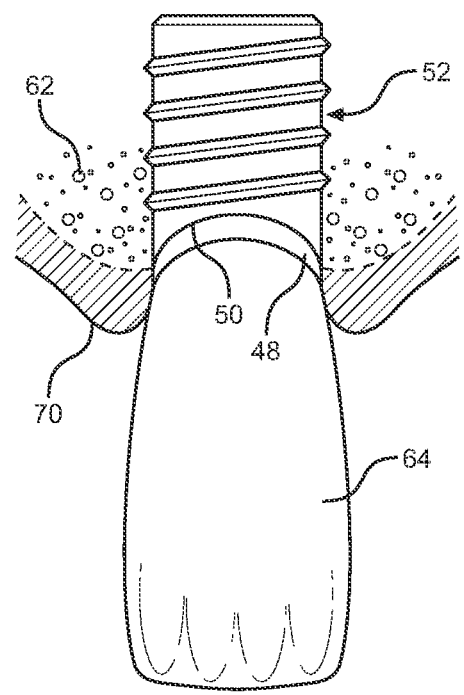

FIGS. 6A-6C illustrate an embodiment of the invention, in which collar 48 of abutment 49 and upper surface 50 of implant 52 have mating surfaces that are not flat, but instead are contoured to adapt to a particular configuration or location in the patient's mouth. The illustrated example relates to an implant system for a front upper tooth 64, where upper surface 50 of implant 52 and the lower surface of collar 48 are contoured with a double curvature profile to adapt to the shape generated by the sum of the curvatures of the bone in the mesial-distal direction and in the labio-lingual direction. The upper surface of collar 48 and the margin of tooth 64 provided as a crown may also be contoured with a double curvature profile to adapt to the shape generated by the sum of the curvatures of the gingiva in the mesial-distal direction and in the labio-lingual direction. The healing cap may also be contoured (for example, milled) to match upper surface 50 of implant 52.

Such custom contouring is facilitated by the availability of CAD-CAM equipment in the dentist's office, as explained in greater detail hereinafter. Data input to a CAD-CAM machine may be provided with a variety of tools, for example, with appropriate computer software receiving input from the dentist.

Also as illustrated in FIGS. 6A-6C and 7, implant system 54 (supporting an artificial front tooth 64) and implant system 56 (supporting an artificial molar 66) can be implanted into a patient such that surfaces 50 and 58 are at or near the surface of the bone (identified in FIGS. 6B and 7 respectively by reference numerals 60 and 62). The upper surfaces of collars 48 or 68 are also at or near the outer surface of the gingiva, indicated respectively by reference numerals 70 and 72.

Referring again to FIG. 3 and to FIGS. 8A-8B, stump 32 may have a longitudinal axis that is coincident with the longitudinal axis of abutment 22, or may have a longitudinal axis that is angled in relation to the longitudinal axis of abutment 74, in the manner of stump 76 in FIGS. 8A and 8B. The use of an angled stump may be particularly useful when the implant system supports an artificial tooth that is placed to have an angled axis in relation to the implant, or when the implant system is disposed at an angled position with respect to the adjacent teeth.

One more advantage of an implant system according to the present invention is that the restoring dentist may determine the appropriate direction for ideal placement of the implant in the bone without considering the angle of the abutment stump in relation to the abutment post (see, for example, stump 76 and post 79 in FIGS. 8A and 8B). The restoring dentist can then mill an abutment 74 from a zirconia block to produce a stump 76 having a desired angle by using a CAD-CAM system adapted for a dental practice and driven by appropriate software, as described hereinbelow. This arrangement provides the dentist with total flexibility by virtually eliminating his inventory of pre-manufactured implants and abutments of different sizes and angles, and by enabling him to manufacture each component of the implant system when needed, for example, to even manufacture an implant at the time of placing the implant into the bone, and an abutment at the time of joining the abutment to the implant, usually months later.

The stump of the abutment may include one or more faces that are generally flat. FIGS. 8A and 8B depict stump 76 having a single flat surface 78, which, when matched with a corresponding flat face within a dental restoration (for example, within an artificial crown) prevents the rotation of the restoration in relation to post 79. This arrangement provides for greater stability of the crown. In situations where stump 76 is angled with respect to the longitudinal axis of post 79, the restoring dentist may rotate abutment 74 within the implant well to improve minor angulations or tooth spacing, until the desired angular position of stump 76 is achieved.

Figure 9:
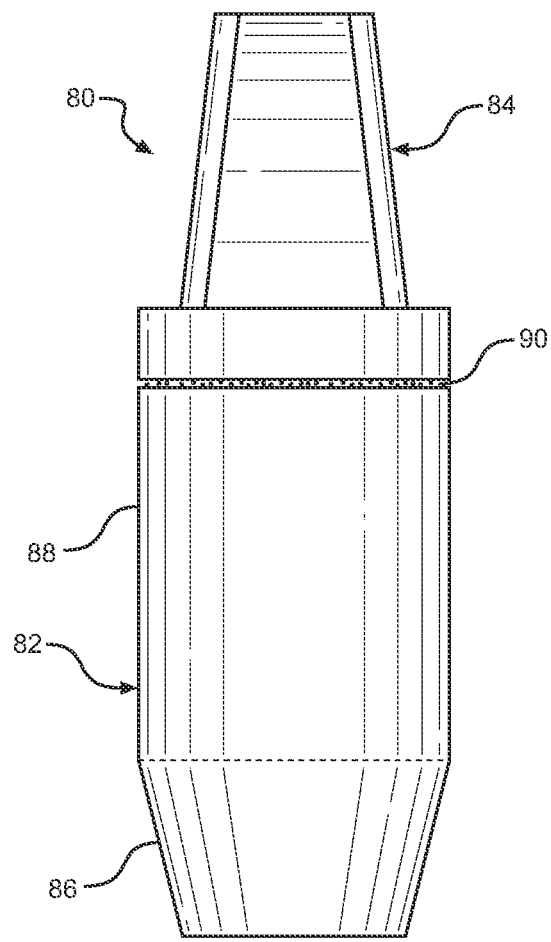
FIG. 9 is a perspective view of another implant system according to the invention.
Figure 10:
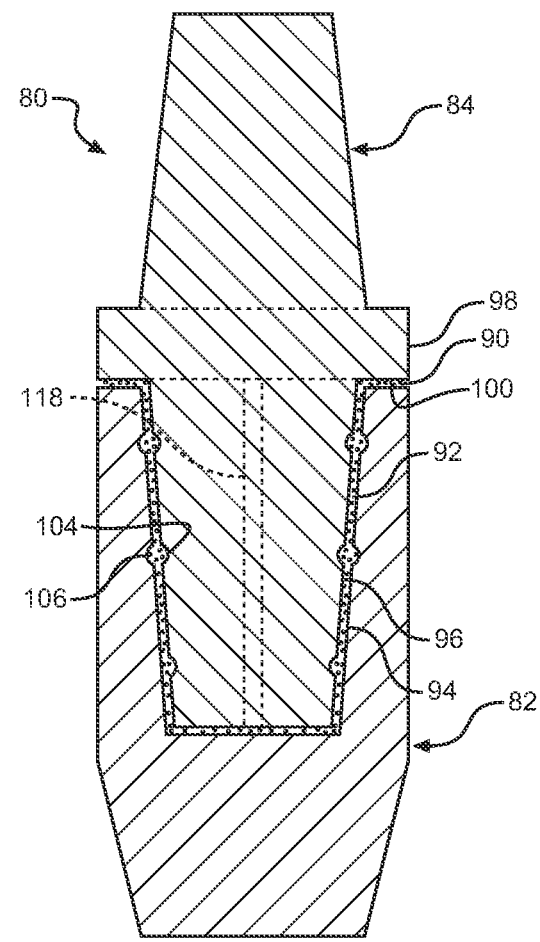
FIG. 10 is a cross-sectional view of the implant system of FIG. 9.

FIGS. 9 and 10 illustrate another embodiment of the invention. Like the previously described embodiments, implant system 80 includes an implant 82 and an abutment 84. Implant 82 has a lower portion 86 that tapers inwardly toward the lower end of implant 82 to prevent an undesired degree of penetration of implant 82 into the patient's bone or into a neighboring bodily cavity (for example, the paranasal sinus). When implant 82 is employed, the alveolar bone of the patient may be drilled with a tapered bit, such that main body 88 of implant 82 cannot move beyond the end of the bored opening since such end has a smaller diameter than main body 88.

Still referring to FIGS. 9 and 10, implant 82 and abutment 84 may be engaged one to the other with a retentive elastomeric material 90, which is disposed in an interstice or gap 92 between implant 82 and abutment 84. In particular, retentive elastomer 90 is disposed in the gap between well 94 and post 96 and between collar 98 and upper surface 100.

Retentive elastomer 90 has resilient (or flexible) properties, such that, after the coupling of abutment 84 with implant 82, abutment 84 retains a limited degree of mobility through compression and expansion of the resilient retentive elastomer. Retentive elastomer 90 may or may not have adhesive properties. The described arrangement enables an artificial tooth supported by abutment 84 to move in a fashion similar to that of a natural tooth. This is an advantageous feature of the invention, because implant systems of the prior art are rigid in relation to the alveolar bone.

In one embodiment of the invention, the resilient retentive elastomer is a silicone or silicone-containing material and may be either mono-component or bi-component, for example, may be an elastomeric material formed from two components (a base resin and a catalyst or curing agent) mixed at the nozzle of a dispenser syringe at the time of application. In another embodiment, the resilient product (for example, silicone) has a composition or includes additives that make it resistant to oral yeast.

Figure 13:
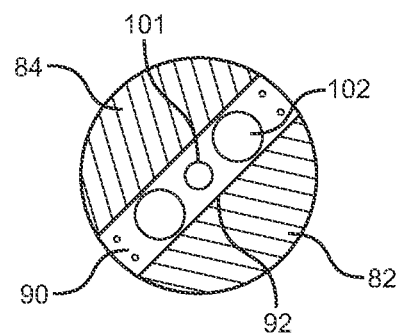
FIG. 13 is detail view of the coupling area between the implant well and the abutment post, in which a retentive elastomeric product containing micro-bubbles and micro-spacers is applied.

Referring to FIG. 13, retentive elastomer 90 incorporates micro-bubbles 101, which may be shaped like small cavities formed within retentive elastomer 90 or like micro-balloons filled with an enduring gas such to favor the above described movement of abutment 84 in relation to implant 82. The enduring gas or the retentive elastomer should be such to prevent dispersion of the gas through retentive elastomer 90, preserving the volume of micro-bubbles 101 over time.

One of the key functions of micro-bubbles 101 is to provide expansion and compressibility within interstice or gap 92. Retentive elastomer 90 may also contain micro-spacer elements that controllably distance well 94 from post 96. Such micro-spacer elements 102 preferably have equal diameters and may be shaped in various shapes, for example, like filled flexible micro-spheres or like micro-rods. The micro-spacers are typically uniform in diameter. The provision of a gap 92 filled with retentive elastomer 90 containing micro-bubbles 101 and micro-spacer elements 102, which insures a controlled spacing between implant 82 and abutment 84 and which allows a relative movement between implant 82 and abutment 84, is another relevant aspect of the present invention.

Retentive elastomer 90 acts as a stress-relieving joint, for example, when the supported restoration is subject to compressive movements during chewing.

Referring again to FIG. 10, one or more grooves 104 may be carved on post 96 transversally to the longitudinal axis of abutment 84. Grooves 104 create one or more annular cavities between post 96 and well 94, which are filled with a retentive product (in one embodiment, with retentive elastomer 90) and increase resistance to extraction of post 96 from well 94 when a tensile strength is applied to abutment 84. In one embodiment, one or more parallel horizontal grooves 104 are provided; in another embodiment, a single spiral groove is provided.

Still referring to FIG. 10, the joining effect between post 96 and well 94 is further increased by providing one or more recesses 106 in well 94, which may or may not be disposed in facing relationship with grooves 104 to jointly create an annular cavity of toroidal shape around post 96. Recesses 106 may be in equal number as grooves 104, or not all of grooves 104 may have a facing recess 106. For example, the lowest groove on post 96 may not have a facing recess, in order to avoid the use of excessive force if the dentist desires to disengage abutment 84 from implant 82, for example, if abutment 84 needs to be replaced or repaired.

Figure 11:
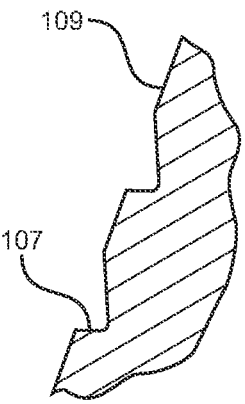
FIG. 11 is s detail view of recesses in the well in a variant of the implant of FIG. 9.

Preferably, recesses 106 are shallow, to facilitate extraction of abutment 84 from well 94. In the embodiment depicted in FIG. 11, recesses 107 are shaped like notches on well 109.

A person skilled in the art will appreciate that grooves 104 and recesses 106 may be provided in a variety of shapes, patterns and numbers, in facing or non-facing relationships, and that, in different embodiments, only grooves 104 may be provided, or only recesses 106, or a combination of both. Moreover, the surfaces of post 96, well 94, upper surface 100 or collar 98 may be treated to increase adhesion and sealing effect, for example, may be etched or sandblasted.

For example, FIG. 12 illustrates another embodiment of the invention, in which abutment 108 includes upper and lower grooves 111 and 113 in facing relationship respectively with upper and lower recesses 115 and 117 on well 112 of implant 114, and central groove 110 that has no corresponding recess. Implant system 80 also includes a collar 116 on abutment 108 that flares upwardly and outwardly, as described hereinabove.

Referring again to FIG. 10, one or more longitudinal grooves 118 may be carved on post 96, which are particularly effective in countering any rotational forces applied on abutment 84. In one embodiment, two longitudinal grooves 118 are defined on post 96 in symmetrical positions. In other embodiments, longitudinal recesses (not shown) may be defined in well 94 instead of longitudinal grooves 118, or both longitudinal grooves 118 and longitudinal recesses may be provided, either in facing relationship or offset one with respect to the other. The anti-rotational effect of longitudinal grooves 118 is particularly important for implant systems supporting artificial front teeth. The longitudinal recesses in well 94 may also be used by the restoring dentist to place the implant in the bone by using a placement tool that has protrusions configured to fit in the recesses on the well, such to grab and rotate implant 82. In this situation, the longitudinal recesses will preferably be semi-cylindrical or have other shapes that are best suited to engage the placement tool. It should be understood in that in different embodiments of the invention only one or more lateral grooves on the abutment post or recesses on the well may be provided, or only one or more longitudinal grooves on the post or recesses on the well, or both.

When retentive elastomer 90 is employed, the presence of grooves 104 and/or recesses 106 creates a sealing ring effect, similar to the effect provided by an O-ring, which creates a mechanical lock between implant 82 and abutment 84. The strength provided by such mechanical lock is such that retentive elastomer 90 may have no chemical or physico-chemical adhesive properties, so that the joint strength may be of purely mechanical nature. It will be within the judgment of the restoring dentist to assess whether retentive elastomer 90 should also have adhesive properties.

Sill referring to FIG. 10, implant 82 and abutment 84 may be manufactured in a dentist's office using a dental CAD-CAM machine controlled by appropriate software. Zirconia blocks suitable for milling may be supplied in a partially sintered or crystallized state and, after milling the zirconia is baked in a special high heat oven to achieve the desired strength. The blocks emerge from the oven sterile, clean, with a good implant surface for bone integration, and ready to be placed.

The zirconia blocks are custom shaped using a CAD-CAM machine in the dentist's office or at an external laboratory. Data input to the CAD-CAM machine is provided via computer instructions.

In a first step of an embodiment of the invention, an advanced system of integration software allows the restoring dentist to design an artificial tooth system on a digital model of the patient by integrating surface data with X-ray data. One producer of such integration software and related X-ray equipment is Sirona Dental Systems, Inc. of Salzburg, Austria and Long Island City, N.Y.

In a second step, using software according to the invention, a computer processor analyzes the surface data and the X-ray data produced in the first step and, based on the anatomy of the mouth of the patient and the configuration of the bone where the implant is to be placed, an implant and an abutment with the desired properties are developed. Such properties include length and diameter of the implant, depth of the implant well, length and taper of the abutment post, numbers and positions of grooves and recesses (if any) on the abutment post and the implant well, diameter, dimensions and shape of the upper surface of the implant (for example, whether flat or curved), height and shape of the abutment collar, height, angle and taper of the stump, and number and position of any flat surfaces on the stump. Therefore, software according to the second step enables the production of a digitally imaged and designed implant system that is customized according to the anatomy and wishes of the patient, and to the judgment of the restoring dentist. Moreover, the implant system may be modified digitally as desired.

Figure 14:
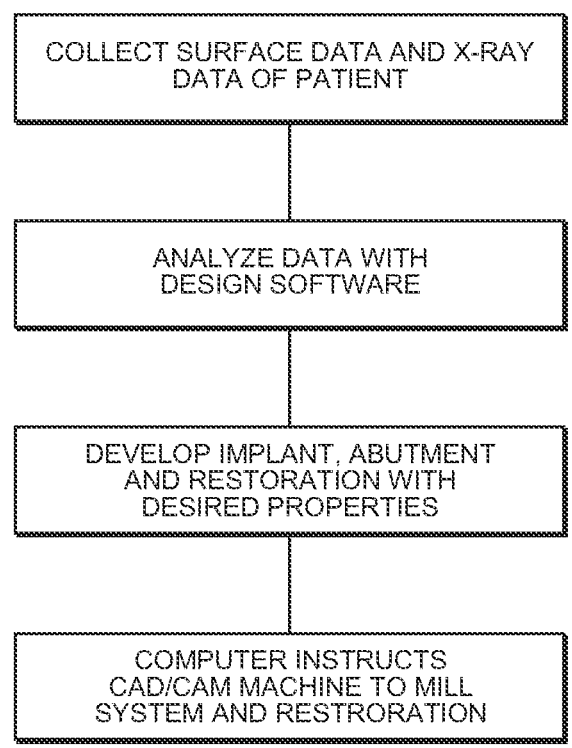
FIG. 14 is a schematic representation of a method of manufacturing a dental system according to the invention, which includes advanced data integration and computer design of the implant, abutment, dental restoration and instructions to CAD/CAM machine.

The developed data are then used to provide CAD/CAM data for a dental milling machine, which manufactures an implant and an abutment having the desired characteristics, in a dental office or in an outside laboratory. Using the above described digitized images and designs and suitable CAD/CAM equipment, the implant and/or the abutment can be produced when needed, at different times if desired, providing the dentist with total flexibility and significantly reduced inventories. The main features of software according to the present embodiment are summarized in FIG. 14.

Figure 15:
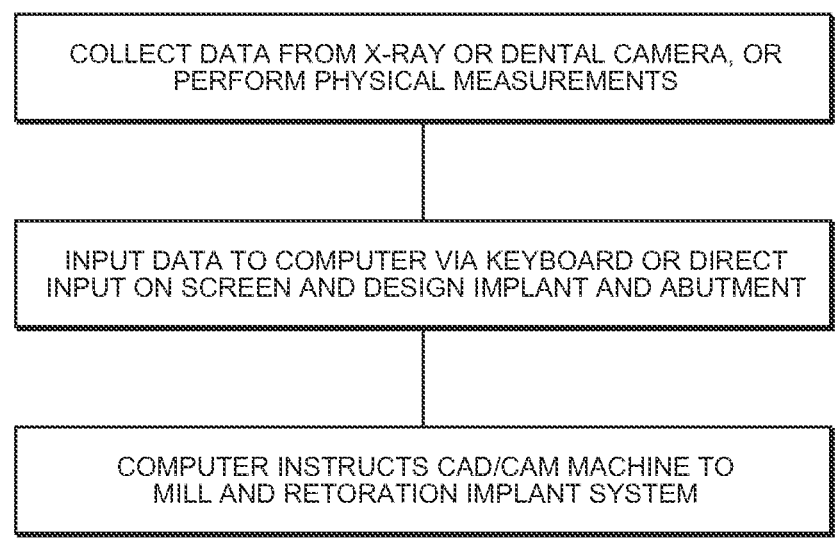
FIG. 15 is a schematic representation of a method of manufacturing a dental system according to the invention, which includes manual data input and computer rendition of the implant, abutment and instructions to CAD/CAM machine.

In another embodiment of the invention, standard input data to the CAD/CAM machine may be provided with different tools and/or methods instead of using the above described integration software, in a manner similar to the tools and methods presently employed to produce dental restorations such as crowns. For example, the restoring dentist may input data at a keyboard or at a screen, filling in choice boxes related to parameters of the implant system such as abutment angle and collar height according to the process summarized in FIG. 15. The input data used by the dentist may be generated from 2-dimensional X-rays, dental cameras, or through direct measurements. Software according to the present invention then provides a three-dimensional image of the implant system and enables the dentist to adjust parameters (for example, the diameter and length of the abutment post) according to his/her professional judgment.

An important feature of the present invention is the ability to generate complementary designs of implant, abutment and supported restoration (for example, of an artificial crown) within narrow tolerance ranges. Starting from X-ray data, the restoring dentist can both develop, and machine in his office to tight tolerances, the implant, the abutment and also the crown, insuring not only a proper anatomical fit of the implant system and restoration within the mouth of the patient, but also a fit among the components of the implant system and restoration within narrow tolerances.

In addition, use of 3D X-ray imaging with the appropriate accuracy enables the design of a root-form implant that can be milled from X-ray data in advance, before a tooth is extracted, and that can be ready for placement after extraction. When placed at extraction, an implant is termed an "immediate implant." The implant, abutment and restoration can also be prepared in advance, and then the implant, abutment and crown are joined one to the other and immediately placed after the tooth is extracted, or are joined one to the other in situ. Joining may be performed using a dental cement, or the implant may be joined to the abutment by providing grooves and/or recesses on the abutment post and/or the implant well and then filling the gap between abutment post and implant well using a retentive elastomeric product as described hereinabove. Alternatively, implant and abutment may be designed and milled as a single piece rather than as two separate pieces.

Alternatively, a tooth may be extracted and the restoring dentist may scan the remaining tooth socket with a dental camera or scan the extracted tooth or an impression of the socket. An implant of appropriate shape is then developed and milled, with a shape that is not cylindrical, but that has a profile matching the shape of the tooth root. The implant may also have an upper surface that is appropriately contoured for best fit with the bone, and the abutment would then have a collar with a lower surface that is appropriately contoured to engage the upper surface of the implant. The implant can be placed in the socket either on the same day as the extraction, or, if not possible, on the following day after cleaning the socket from blood clots that may have formed. As mentioned, implant and abutment may be manufactured as separate pieces or as a single piece and subsequently placed.

In a method of use of a dental implant system according to the invention, a restoring dentist initially drills an opening in the bone of the patient that has a diameter suited for the insertion of an implant, as it is known in the art. The opening may be drilled with a beveled bit, in order to have a tapered end of the opening, or with a straight outer wall for a sinus lift procedure.

When it is desired to avoid a penetration of the implant into the bone beyond a certain depth (for example, when a bone of limited thickness divides the mouth from a bodily cavity such as the paranasal sinus), an implant such as implant 82 of FIGS. 9 and 10 is used. Lower portion 86 of implant 82 will then be received in the tapered end of the opening.

Implant 82 is joined to the surrounding bone according to a method known in the art. In particular, implant 82 may be provided with a spiral, screw-like thread on its outer surface and be screwed into the opening, or may be simply passively placed in the bone for integration over a period of time. In that case, the restoring dentist covers well 94 with a cover or healing cap and stitches the surrounding gum tissue over or around the healing cap, or reduces the cap and sutures over it.

In one embodiment, the cover or healing cap includes a stem portion that is inserted within well 94, and a hemispherical or cylindrical cap portion configured to rest on the upper surface 100, covering well 94. Before inserting the cover or healing cap, the restoring dentist may apply an antibiotic product within well 94. In addition, the cover or healing cap may be constructed to elute a desired product (e.g. an antibiotic) over time.

The healing cap may be specially contoured to snap into well 94. For example, the healing cap may include semi-cylindrical longitudinal protrusions that engage semi-cylindrical longitudinal recesses in well 94, and may be provided in standard sizes or be specially machined to the desired shape.

Implant 82 is prepared before the implant procedure by using a CAD-CAM system and software as described hereinabove. Abutment 84 can also be prepared ahead of time using software as described hereinabove, and both implant 82 and abutment 84 may include constructive features (such as horizontal and vertical grooves in the well and on the post) as desired by the restoring dentist, as well as ridges on the outer surface of the implant.

Implant 82 is placed first, covered with a healing cap, and after integration and healing, implant 82 is uncovered and the healing cap is removed. A retentive elastomer product or a dental cement is applied within the well, in sufficient quantity to insure a proper filling of gap 92, including any horizontal or vertical grooves that may be present and also including the interstice between collar 98 and upper surface 100. Preferably, the restoring dentist applies a resilient retentive elastomer that contains micro-bubbles as well as micro-spacers of equal diameter to enable a relative movement of abutment 84 in relation to implant 82 and to insure a uniform thickness of gap 92. For example, the restoring dentist may inject a bi-component, Candida-resistant silicone retentive elastomer containing both micro-bubbles and flexible micro-spacers using a double-barreled syringe, in which two resin components (a base product and a catalyst or curing agent) become mixed at the nozzle.

Finally, the artificial tooth or bridge is affixed to the abutment.

The present invention also enables a restoring dentist to prepare an implant, abutment and restoration (for example, a crown) in the dental office by using CAD/CAM equipment programmed by using 3-dimensional X-ray data of the patient, as described hereinabove. Implant, abutment and crown may be placed during a single session and movement of the crown before osseo-integration of implant 82 may be prevented by stabilizing the crown in place bonding it to the adjacent teeth with a dental cementing agent (known in the trade as a luting agent).

In particular, an immediate implant system can be created, shaped to tight tolerances to match the socket of an extracted tooth by scanning the tooth or tooth socket or an impression of the tooth socket after extraction, or by using 3-dimensional images of the tooth structure before extraction. In that scenario, the restoring dentist will shape the implant system (particularly the outer and upper surfaces of the implant) to reflect socket or tooth root configuration, and implant passively an implant shaped to have a divergent profile that closely resembles the socket or the root area of the extracted tooth.

The preceding description has illustrated a number of advantages of an implant system according to the present invention, some of which include:

1. A healthy emergent profile of the implant system and of the crown carried by the implant system.
2. A stress-relieving joint when implant and abutment are joined with a retentive elastomeric product, which acts as a shock absorber.
3. Customization through a CAD-CAM system, which allows an essentially perfect tailoring of the implant system to patient anatomy, and which enables an inventory reduction of finished product on an as needed basis.
4. Non-toxicity due to the use of zirconia or other biocompatible ceramic material.
5. No electro-negativity due to the use of ceramic products.
6. No screws or joints that leak, harbor bacteria or break.
7. The entire implant system (implant and abutment) can be colored white or off-white for best cosmetic results. This makes the implant system less noticeable when placed in a thin bone or front mouth area.
8. In-office milling allows for design flexibility, greatly increasing the usefulness of the implant and implant system per se, and the creativity of the restoring dentist.
9. The entire implant system, which supports the dental restoration, can be milled from the same ceramic product, customizing size and shape of the implant, and the abutment can be designed for the needed height, angle of divergence and diameter.
10. A tooth form implant, abutment and restoration can be milled at the same time, even before a tooth is extracted, and can be shaped to match the tooth socket.
11. The abutment can be attached to the implant with an interstitial retentive elastomer that maintains an even gap thickness. This thickness, in turn, allows a degree of movement of the artificial tooth.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

The invention claimed is:

1. A dental implant system comprising:
    an implant having an outer surface, an inner surface, and an upper surface annularly connecting the outer surface to the inner surface, the inner surface defining a well projecting from the upper surface into the implant, the implant being monolithic and made from a millable ceramic; and
    an abutment having a post, a stump, and a collar, the post having a shape configured to engage the well while leaving a gap therebetween, the stump and the collar being configured to support a dental restoration, the collar extending outwardly from the abutment at a transition between the post and the stump and having a lower outer perimeter substantially equal to an outer perimeter of the upper surface of the implant, the abutment being made from the millable ceramic,
    wherein one or more grooves are defined in a wall of the post and one or more recesses are defined in a wall of the well extending perpendicular to the longitudinal axis of the post, and
    one or more grooves are defined in the wall of the post and one or more recesses are defined in the wall of the well extending substantially parallel to the longitudinal axis of the post.

2. The implant system according to claim 1, wherein the millable ceramic comprises zirconia.

3. The implant system according to claim 1, wherein the collar has one or more of variable thickness or width.

4. The implant system according to claim 1, wherein at least one of,
    the upper surface of the implant and a bottom surface of the collar, or
    an upper surface of the collar and a margin of the dental restoration, are shaped with matching curved surfaces.

5. The implant system according to claim 1, wherein the well and the post have parallel frustoconical shapes.

6. The implant system according to claim 1, further comprising a retentive elastomeric product to be disposed in the gap.

7. The implant system according to claim 6, wherein the retentive elastomeric product has micro-bubbles therein such to provide elasticity and compressibility within the gap.

8. The implant system according to claim 6, wherein the retentive elastomeric product further comprises micro-spacers such to provide a distance between the well and the post.

9. The implant system according to claim 8, wherein the micro-spacers are of substantially equal diameter.

10. The implant system according to claim 6, wherein the retentive elastomeric product comprises an elastomeric product that is resistant to one or more of biological or mechanical degradation.

11. The implant system according to claim 1, further comprising a computer-readable medium carrying one or more sequences of instructions for manufacturing the dental implant system, wherein execution of the one or more sequences of instructions by one or more processors causes the one or more processors to perform the steps of:
    analyzing surface data and X-ray data to produce a three-dimensional model of a jaw and a tooth of a patient;
    developing contour data of the implant and of the abutment suited for an anatomy of the patient; and
    producing machine data for milling the implant and the abutment from blocks of the millable ceramic.

12. The implant system according to claim 1, further comprising a healing cap configured to cover the implant after placement in a patient during a period of integration of the implant within a bone of the patient, wherein the healing cap is configured to release an antibiotic composition.

13. The implant system according to claim 1, wherein the collar is shaped to have an upper outer perimeter configured to match a transverse anatomical profile of a natural tooth.

14. The implant system according to claim 1, wherein the outer perimeter of the upper surface of the implant is shaped to conform to a surrounding bony ridge of a jaw, and wherein the collar has a variable height set to provide optimal position in relation to a gingival crest and to improve cosmetic appearance.

15. The implant system according to claim 1, wherein the collar has a flaring lateral surface.

16. The implant system according to claim 1, wherein a lowest groove in the wall of the post has no facing recess, such to decrease an amount of force required by a dentist to extract the post from the well.

17. The implant system of claim 1, wherein there are a plurality of grooves and a plurality of recesses disposed in the wall of the post and in the wall of the well, and wherein at least some of the plurality of grooves and of the plurality of recesses are disposed respectively to be in facing relationship to one another when the post engages the well.

* * * * *